(12) United States Patent
Bays et al.

(10) Patent No.: US 6,423,078 B1
(45) Date of Patent: Jul. 23, 2002

(54) DERMABRASION INSTRUMENT, INSTRUMENT ASSEMBLY AND METHOD

(75) Inventors: F. Barry Bays, Arlington, TN (US); Gary Peters, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 09/544,264

(22) Filed: Apr. 6, 2000

Related U.S. Application Data

(60) Provisional application No. 60/130,655, filed on Apr. 23, 1999.

(51) Int. Cl.[7] ............................................... A61B 17/50
(52) U.S. Cl. ....................................................... 606/131
(58) Field of Search ................................ 606/131, 133, 606/170, 180, 80, 84, 85; 132/73.6, 74.5, 75.6, 75.8, 76.4

(56) References Cited

U.S. PATENT DOCUMENTS

| | | | |
|---|---|---|---|
| 2,429,356 A | * 10/1947 | Hicks | 606/180 |
| 5,269,785 A | * 12/1993 | Bonutti | 606/80 |
| 5,456,689 A | * 10/1995 | Kresch et al. | 606/180 |
| 5,707,383 A | 1/1998 | Bays et al. | |
| 5,782,795 A | * 7/1998 | Bays et al. | 606/180 |
| 6,214,009 B1 | * 4/2001 | Toriumi et al. | 606/80 |

* cited by examiner

Primary Examiner—Eduardo C. Robert

(57) ABSTRACT

A dermabrasion instrument includes an outer member and an inner member rotatably disposed in the outer member with an abrading member of the inner member exposed from the outer member. An aspirating passage in the abrading member establishes communication with an aspirating channel of the inner member from externally of the abrading member so that debris from abrasion of the skin by the abrading member is evacuated through the inner member. The outer member may include a shield disposed over the abrading member to contain the debris. The instrument may include an irrigating port for discharging irrigating fluid adjacent the abrading member. A dermabrasion instrument assembly includes an abrading instrument releasably coupled to a powered surgical handpiece. The instrument has an aspirating channel and the handpiece has a suction port connectible with a source of suction to effect evacuation of debris through the abrading instrument and the handpiece. A method of dermabrasion includes the steps of rotating an inner member of an abrading instrument within an outer member of the instrument to rotate an abrading member of the inner member, abrading the skin with the rotating abrading member and aspirating debris from abrasion through the inner member.

39 Claims, 3 Drawing Sheets

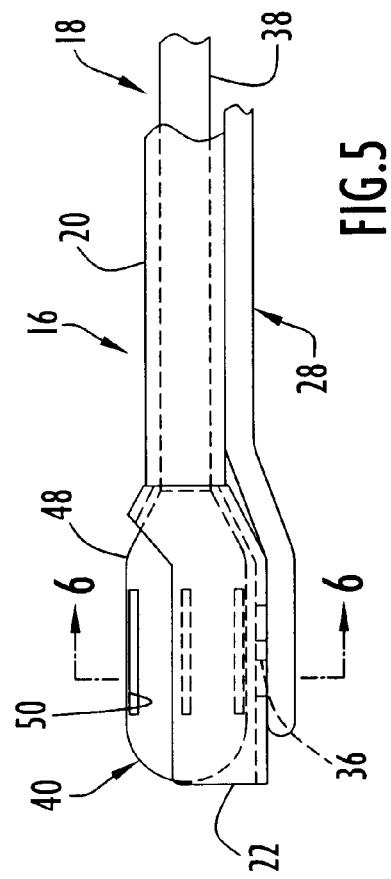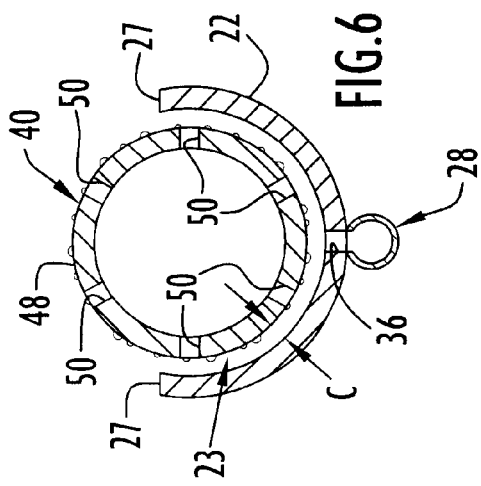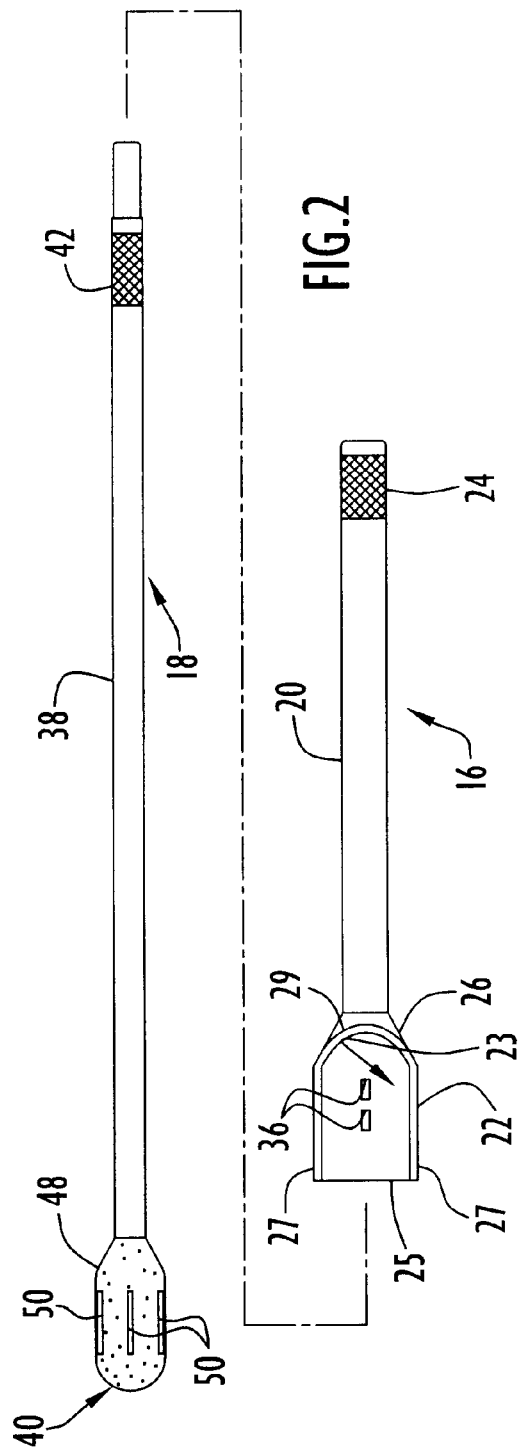

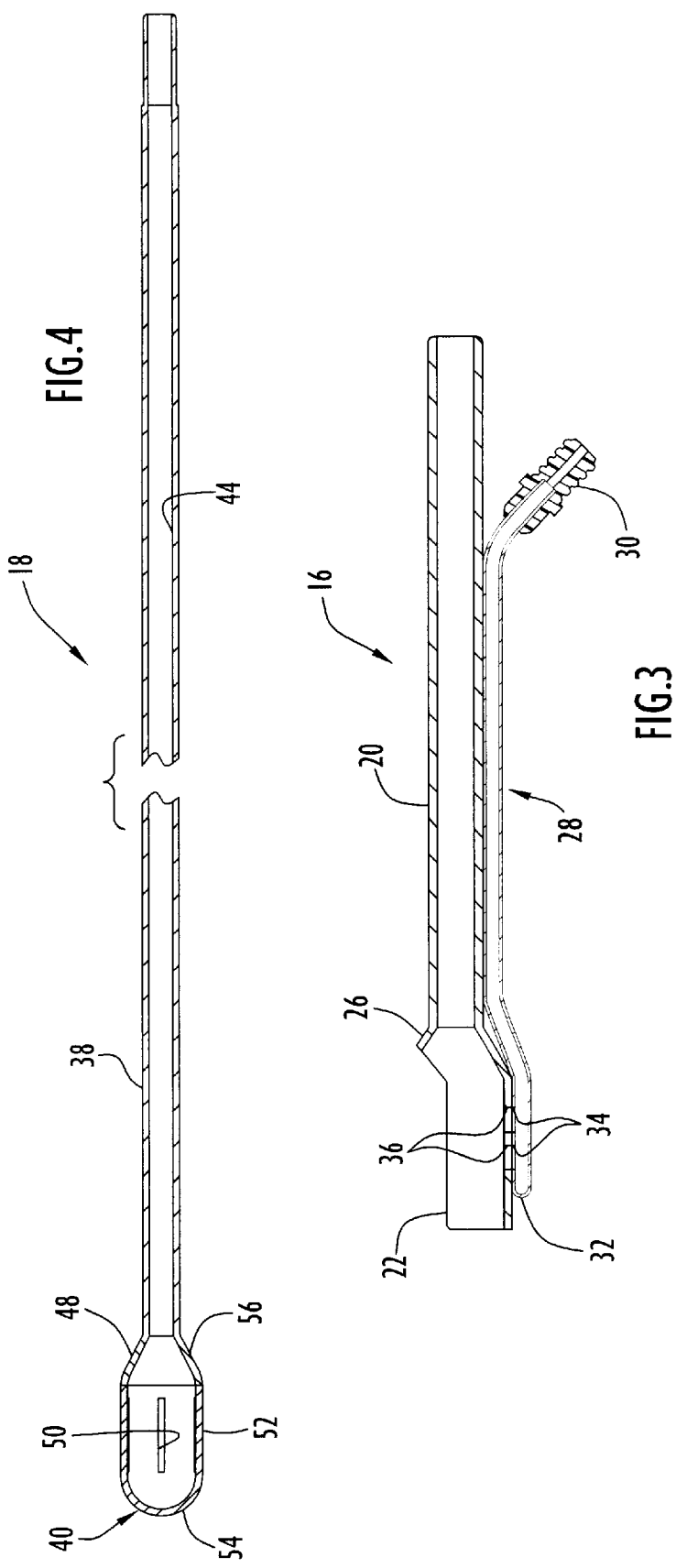

DERMABRASION INSTRUMENT, INSTRUMENT ASSEMBLY AND METHOD

CROSS-REFERENCE TO RELATED PATENT APPLICATION

This application claims priority from prior provisional patent application Ser. No. 60/130,655 filed Apr. 23, 1999, the disclosure of which is incorporated by reference.

BACKGROUND OF THE INVENTION

1. Field of the Invention

The present invention relates to instruments, instrument assemblies and methods for abrasively removing the surface layer of the skin to treat various surface defects therein and, more particularly, to dermabrasion instruments, instrument assemblies and methods wherein the dissemination of debris is avoided.

2. Brief Discussion of the Related Art

Abrasively removing the external surface layer of skin has been used to treat various surface defects in the skin. Removal of the surface layer of the skin by high-speed sanding is referred to as dermabrasion or surgical planing of the skin. During a typical dermabrasion procedure, the surface layer of the skin is removed using an abrading instrument with a rotating abrading member, typically a diamond fraise or wire brush rotated at high speed.

Abrasive methods can be used effectively for scar revision, tattoo removal, skin biopsy, wrinkle reduction and keratosis, for example. Dermabrasion is a preferred treatment for various types of acne scars. It is particularly effective for removing or reducing scars having a saucer or piepan contour, i.e., broad, relatively shallow scars with either tapering edges or a small drop-off between the edges and the floor of the scar. Dermabrasion is also highly effective in eliminating or reducing facial wrinkles, particularly around the mouth.

Conventional abrading instruments, instrument assemblies and methods have numerous disadvantages, however. A primary disadvantage is that the rotating abrading member disseminates or throws skin debris about the operating room making a mess and creating contamination problems for medical personnel. The problem of dissemination of skin debris is exacerbated due to the skin debris being relatively dry and, therefore, more likely to be thrown or scattered about. Other disadvantages include the inability to aspirate or remove skin debris from a dermabrasion site through the abrading instrument, the lack of active cooling of the rotating abrading member and the potential for clogging of the abrading instrument.

U.S. Pat. No. 5,707,383 discloses a surgical abrading instrument used to remove soft tissue in the middle ear. The surgical abrading instrument includes an abrading member mounted on a shaft having a proximal end connectible with a motorized handpiece used to rotate the shaft and, therefore, the abrading member. The dissemination of debris about the operating room is not a problem since the abrading member is used inside the ear.

SUMMARY OF THE INVENTION

Accordingly, a primary object of the present invention is to overcome the aforementioned disadvantages of conventional abrading instruments, instrument assemblies and methods of dermabrasion.

Another object of the present invention is to prevent skin debris from becoming scattered during a dermabrasion procedure by containing the skin debris at the dermabrasion site.

It is another object of the present invention to remove skin debris from a dermabrasion site in a controlled manner during a dermabrasion procedure.

A further object of the present invention is to wet skin debris in a dermabrasion procedure to promote containment of the skin debris.

It is also an object of the present invention to remove skin debris from a dermabrasion site through an abrading instrument performing the dermabrasion.

An additional object of the present invention is to actively cool an abrading member of an abrading instrument during a dermabrasion procedure.

The present invention has as another object to avoid clogging of an abrading instrument during a dermabrasion procedure.

Some of the advantages of the present invention are that the abrading instrument can be used with various conventional powered surgical handpieces to form an instrument assembly, the abrading member can have various configurations, abrasiveness can be imparted to the abrading member in various different ways, the abrasiveness of the abrading member can be varied to provide optimal abrasiveness for particular dermabrasion procedures, contamination problems for operating personnel are greatly reduced, the breathing in of debris by operating personnel is avoided, an air filtration system in the operating room for containment of debris is not needed, and the dermabrasion procedure can be performed as an out-patient procedure.

These and other objects, advantages and benefits are achieved with the present invention as generally characterized in a dermabrasion or abrading instrument for surgical abrasion of a surface of the skin and including an outer member and an inner member rotatably disposed in the outer member with an abrading member or tip of the inner member exposed from the outer member. The abrading member is adapted to abrade a surface of the skin with which the abrading member is contacted while being rotated relative to the outer member. The inner member includes a shaft and the abrading member disposed at a distal end of the shaft. The shaft has a lumen therethrough, and the abrading member has an aspirating passage establishing communication with the lumen from externally of the abrading member. The lumen is connectible with a source of suction to draw debris, produced by abrasion of the surface of the skin, into the aspirating passage for removal through the lumen. In a preferred abrading instrument, the outer member includes a shield covering a portion of the abrading member to contain dissemination of the debris due to centrifugal force of the abrading member. An optional irrigating port can be provided in the instrument to discharge an irrigating fluid toward the abrading member whereby the debris is wetter to promote containment thereof.

A dermabrasion or abrading instrument assembly according to the present invention is generally characterized in an abrading instrument and a powered surgical handpiece. The abrading instrument includes an outer member and an inner member rotatably disposed in the outer member with an abrading member or tip of the inner member exposed from the outer member. The inner member includes a shaft and the abrading member disposed at a distal end of the shaft. The shaft has a lumen therethrough in communication with an aspirating passage in the abrading member. The abrading member is adapted to abrade a surface of the skin contacted by the abrading member while the abrading member is rotated relative to the outer member. The powered surgical handpiece is releasably connectible with the inner and outer members to rotate the inner member relative to the outer member. The handpiece includes a suction port connectible with a source of suction to establish suction in the lumen of the shaft by which debris, generated from abrasion of the skin, is drawn into the aspirating passage for evacuation through the shaft and the handpiece.

A method of dermabrasion according to the present invention includes the steps of rotating an inner member of an abrading instrument within an outer member of the abrading instrument to rotate an abrading member or tip of the inner member that is exposed from the outer member, contacting a surface of the skin with the rotating abrading member, abrading the surface of the skin with the abrading member and aspirating debris, produced by abrasion of the skin, through the inner member. A preferred method includes the steps of containing the debris with a shield of the outer member. Optionally, the dermabrasion method includes the step of wetting the debris.

The foregoing and other objects and advantages can be accomplished individually or in combination using the dermabrasion instrument, instrument assembly and method according to the present invention. Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

FIG. 2 is an exploded top view of the abrading instrument shown in FIG. 1.

FIG. 3 is a side sectional view of the outer member of the abrading instrument shown in FIG. 1.

FIG. 4 is a side sectional view of the inner member of the abrading instrument shown in FIG. 1.

FIG. 5 is an enlarged fragmentary view of the distal end of the abrading instrument shown in FIG. 1.

FIG. 6 is a sectional view of the abrading instrument taken through line 6—6 in FIG. 5.

DESCRIPTION OF THE PREFERRED EMBODIMENTS

Figure 1:
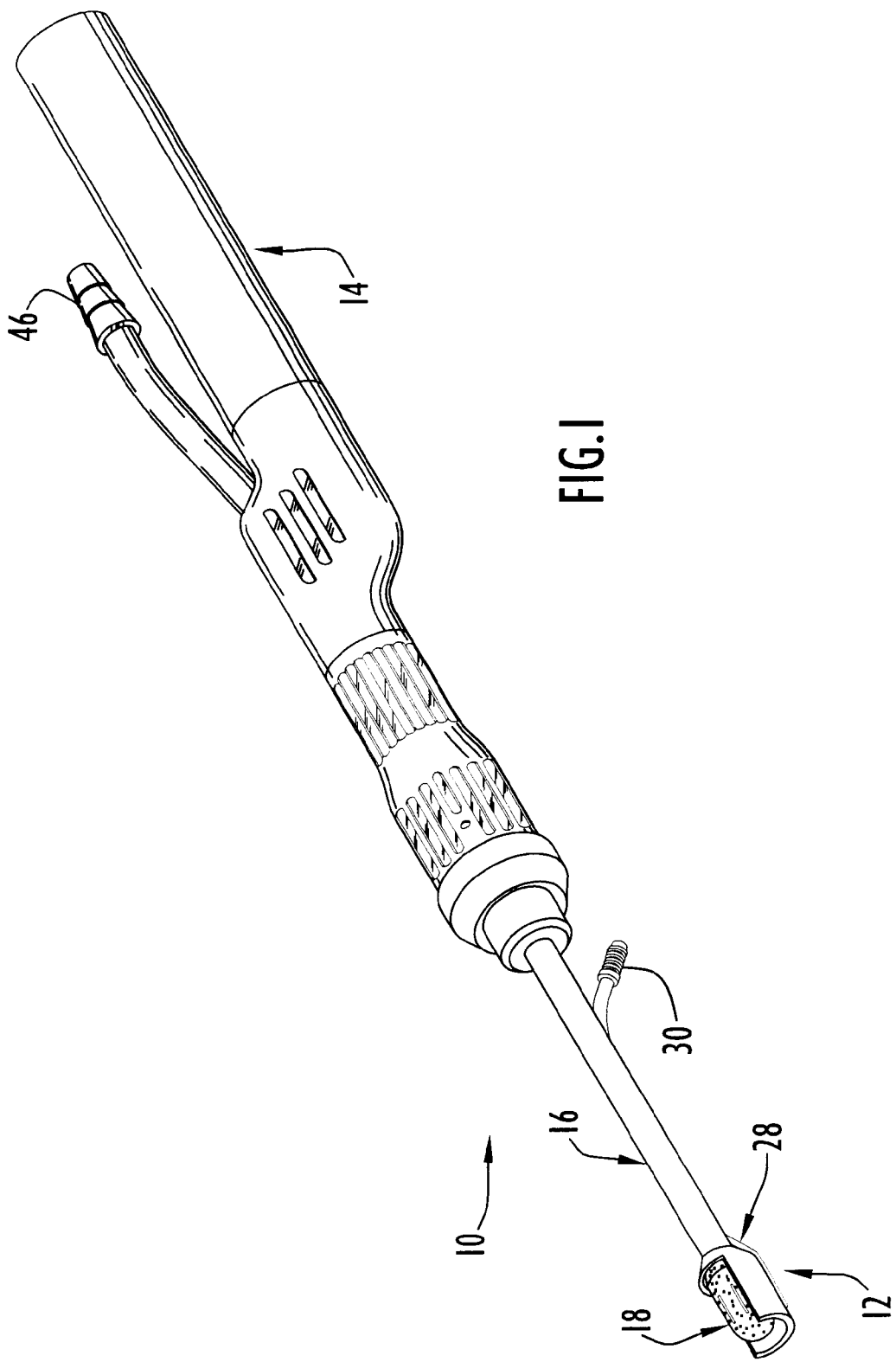
FIG. 1 is a front perspective view of an abrading instrument according to the present invention mounted on a powered surgical handpiece to form an abrading instrument assembly.

A dermabrasion or abrading system or instrument assembly 10 according to the present invention, as illustrated in FIG. 1, includes a dermabrasion or abrading instrument or abrader 12 attached to a powered surgical handpiece 14. Abrading instrument 12 includes an outer member 16 which is held stationary by the handpiece 14 and an inner member 18 which is disposed at least partly within the outer member and rotated by the handpiece to remove the surface layer of the skin. Skin debris generated during a dermabrasion procedure is contained at the surgical or dermabrasion site by the outer member and is drawn into the inner member for removal from the site when a source of suction is connected to the handpiece. While a particular handpiece is shown, it will be appreciated that the abrading instrument can be configured for use with any conventional powered surgical handpiece.

As best seen in FIG. 2, outer member 16 includes an outer tubular member or outer shaft 20 and a shield 22 mounted at a distal end of the outer shaft. Outer shaft 20 is of hollow, cylindrical configuration to define a lumen therethrough and has a knurled surface 24 at a proximal end thereof for receiving a hub (not shown) of the type which releasably mounts a powered surgical handpiece in a stationary manner. Shield 22 includes an arcuate member connected to the distal end of outer shaft 20 by a generally frustoconical flange or shoulder 26 of increasing diameter in the distal direction. As shown in FIG. 4, the distal and proximal ends of outer shaft 20 are open, with the open distal end thereof communicating with the interior of shield 22. In particular, the open distal end of outer shaft 20 opens into the interior of the frustoconical shoulder 26 and communicates with the space 23 defined by the arcuate member, the interior of shield 20 being defined by the space 23 and the interior of sholder 26. As shown in FIGS. 1 and 2, a distal end of shield 22 is open to the space 23 and is defined by an arcuate distal edge 25 of the arcuate member. The shield has straight side edges 27 extending proximally from opposite ends, respectively, of the arcuate distal edge 25 and has an arcuate proximal edge 29. The arcuate proximal edge 29 is disposed at an angle to the side edges 27 and has opposite ends connected to the side edges 27, respectively. The side edges 27 extend parallel to a central longitudinal axis of the outer member 16. The open distal end of shield 22 and the open proximal end of outer shaft 20 define distal and proximal ends, respectively, for the outer member 16.

Referring to FIG. 3, an optional irrigating tube, port or channel 28 is shown extending conformingly along an outer surface of outer member 16 from a coupling 30 at a proximal end of tube 28 to a closed distal end 32 disposed along the arcuate member of shield 22, the distal end 32 being disposed near the distal end of shield 22. Coupling 30 forms an acute angle with the outer member relative to the proximal direction and is shown as a hose adapter which can be connected with a source of irrigating fluids (not shown). For example, the hose adapter can be connected to an end of a length of flexible tubing carrying irrigating fluid from the irrigating fluid source. At least one and, preferably, a pair of irrigating outlets 34, are formed in tube 28 near its distal end 32 in alignment with one or more irrigating inlets 36 formed in shield 22 to permit an irrigating fluid such as water to flow from the irrigating tube 28 toward an abrading member or tip of the instrument and toward a dermabrasion site via the shield so as to cool the abrading member and improve debris containment by wetting the skin debris. The irrigating tube is fixedly attached to the outer member, for example by laser welding the tube to the outer member at a plurality of locations.

Referring again to FIG. 2, it can be seen that inner member 18 includes an inner tubular member or inner shaft 38 and the abrading member or tip 40 mounted at a distal end of the inner shaft 38. Inner shaft 38 is tubular or of hollow, cylindrical configuration with a knurled surface 42 at a proximal end thereof for receiving a hub (not shown) of the type which can be releasably mounted for rotation by the powered surgical handpiece. Inner shaft 38 is configured to fit telescopically within outer shaft 20 and, as best seen in FIG. 4, the inner shaft 38 is of hollow, cylindrical configuration with open distal and proximal ends to define an aspirating or suction channel, passage or lumen 44 along its length which communicates with a source of suction via a coupling 46 on handpiece 14 when the abrading instrument is attached to the handpiece as shown in FIG. 1. Abrading member or tip 40 is a hollow member defining or enclosing an interior in communication with the aspirating channel 44. Abrading tip 40 has an abrasive outer surface 48 and one or more aspirating passages, ports or openings 50 formed through the abrasive surface. In the case of abrading instrument 12, the abrasive outer surface 48 extends along or covers the entire exterior of tip 40. The aspirating passages 50 establish communication with the aspirating channel 44 from externally of the abrading tip so that skin debris can be drawn into the channel 44 via the aspirating passages 50 and the interior of the abrading tip for removal from the surgical or dermabrasion site. The abrading tip shown in FIG. 4 includes a hollow, cylindrical central portion 52 of larger diameter than inner shaft 38, a closed distal end defined by a rounded or hemispherical end wall 54 and an open proximal end defined by a tapered or frustoconical proximal portion 56 of decreasing diameter in the proximal direction. The cylindrical central portion 52 extends proximally from the rounded end wall 54, and the tapered proximal portion 56 extends proximally from the cylindrical central portion to the distal end of inner shaft 38. Aspirating passages 50 in the abrasive outer surface of the tip are shown as a plurality of longitudinal slots formed in the cylindrical portion 52 of the tip at angularly spaced locations about the circumference of the cylindrical portion. As shown in FIGS. 2 and 4, the slots extend longitudinally along the central portion 52 and are parallel to one another and to a central longitudinal axis of inner member 18. The closed distal end of the abrading tip 40 and the open proximal end of inner shaft 38 define distal and proximal ends, respectively, of the inner member 18.

Abrading instrument 12 can be assembled by inserting the proximal end of inner member 18 into the open distal end of outer member 16 and sliding the inner shaft into the outer shaft until the abrading tip 40 is disposed in the interior of the shield 22 and abuts the frustoconical flange 26 of the shield 22. Appropriate hubs can then be mounted at the proximal ends of the inner and outer members, respectively, to permit the abrading instrument to be attached to a powered surgical handpiece. In the assembled condition or state, as shown in FIGS. 1, 5 and 6, inner shaft 38 is disposed telescopically within outer shaft 20 thereby positioning abrading tip 40 concentrically within shield 22 with a small radial clearance C therebetween to prevent the abrasive surface of the abrading tip from contacting the inner surface of the shield when the tip is rotated relative to or within the shield. The abrading tip is disposed alongside the shield with a portion of the tip covered by the shield and another portion of the tip exposed from the shield to enable contact of the abrasive surface with a surface of the skin. The irrigating outlets are disposed adjacent the abrading tip so that irrigating fluid discharged therefrom is directed or discharged toward the tip. The shield is disposed between the irrigating tube and the tip with the irrigating inlets of the shield aligned with the irrigating outlets of the irrigating tube. As shown in FIG. 5, aspirating passages 50 on the side of the abrading tip are longitudinally aligned with the irrigating inlets 36 formed in the shield so that at least some of the irrigating fluid flows into the aspirating passages to help clear the aspirating passages of skin debris. In other words, aspirating passages 50 are disposed at the same or substantially the same longitudinal location as irrigating inlets 36 when the inner member 18 is inserted in the outer member 16 in the assembled condition.

The frustoconical flange 26 of shield 22 defines a mechanical stop or abutment surface which receives the proximal portion 56 of the tip 40 to limit or prevent the inner member from moving longitudinally, proximally relative to the outer member during operation so that the aspirating passages remain substantially in alignment with the irrigating inlets. As best seen in FIG. 6, shield 22 extends at least about 180 degrees around tip 40 so that portions of the abrasive surface facing the user are covered during use. In the case of abrading instrument 12, the shield 22 extends slightly greater than 180 degrees around the tip 40 as seen in FIG. 6. For maximum coverage, shield 22 can be configured to extend distally beyond the rounded end wall 54 of the tip as shown in FIG. 1. Exposed portions of the tip, i.e., portions of the tip exposed from or not covered by the shield 22, can then be used to surgically abrade or remove the surface layer of the skin. The rounded end wall 54, cylindrical central portion 52 and frustoconical proximal portion 56 of the tip define multiple abrasive planes which can be used to sculpt the outer layer of the skin when the inner member is rotated during a dermabrasion procedure. The frustoconical flange 26 can be notched, cut out or shaped on the side that is contiguous with the side edges 27 to expose a greater portion of the frustoconical proximal portion 56 of the tip for maximum flexibility of use. In the case of abrading instrument 12, for example, the angle of the proximal edge 29 results in greater exposure of the proximal portion 56. Since the distal end of the shield is open, the distal end of the tip is also exposed for use.

The abrading instrument is releasably attached to the powered surgical handpiece 14 to form a dermabrasion or abrading system or instrument assembly as shown in FIG. 1 by coupling the hubs of the inner and outer shafts, respectively, with mating portions of the handpiece such that the outer member 16 is held stationary by the handpiece and the inner member 18 is rotated by the handpiece within the stationary outer member. Attachment of inner member 18 to handpiece 14 also places the aspirating lumen 44 of the inner member in fluid communication with suction port 46 on the handpiece so that a negative pressure can be created in the aspirating lumen simply by attaching a suction line to the handpiece suction port. If desired, an irrigating fluid can be supplied to the abrading tip via irrigating tube 28 by connecting a hose, tubing, or the like to coupling 30 at the proximal end of the irrigating tube.

A typical dermabrasion or skin abrading method or procedure according to the present invention involves numbing the skin of a patient with a local anesthetic and removing the surface layer of the skin using abrading instrument 12. Removal of the surface layer of the skin is accomplished by rotating inner member 18 relative to outer member 16 to cause tip 40 to rotate within shield 22 and placing the rotating tip against the skin with the shield disposed between the tip and the user, i.e. the person performing the dermabrasion on the patient. The speed of rotation of the tip can be fixed or controlled by the user using a foot pedal or controls on the handpiece. Abrading tip 40 generates debris as the surface layer of the skin is removed, the debris generally flying off the tip in a radial direction due to the centrifugal force generated by rotation of the tip; however, the placement of shield 22 between the tip and the user tends to contain the debris at the surgical or dermabrasion site adjacent aspirating passages 50 in the abrasive surface of the tip. Connection of the handpiece with a source of suction causes the debris to be drawn into the interior of the tip via the aspirating passages 50 for removal through the aspirating lumen of the inner member. Containment of skin debris at the surgical site can be further enhanced by connecting the abrading instrument to a source of an irrigating fluid so that irrigating fluid is supplied at the abrading tip, via the irrigating outlets 34 in irrigating tube 28 and the irrigating inlets 36 in shield 22, to wet the skin debris. More particularly, the irrigating fluid is discharged from the irrigating inlets 36 toward the abrading tip and the site of dermabrasion. The aspirating passages 50 and the irrigating fluid also effect cooling of the abrading tip for improved results. Also, the aspirating passages 50 move past the irrigating inlets 36 as the tip is rotated within the shield, and the irrigating fluid discharged from inlets 36 helps keep the passages 50 free from clogging. Some of the irrigating fluid is drawn into the interior of the tip via the passages 50 for removal through the lumen of the inner member, thusly enhancing aspiration of the skin debris from the surgical or dermabrasion site and inhibiting build up of skin debris in the passages 50. The dermabrasion instrument, instrument assembly and method according to the present invention can be used for a number of purposes including, but not limited to, scar revision, skin biopsy, wrinkle reduction and keratosis. Generally, such procedures can be performed on an outpatient basis.

In an exemplary embodiment, the overall length of outer member 16 is about 2.95 inches and the overall length of inner member 18 is about 4.62 inches, with outer shaft 20 being formed of type 304L stainless steel tubing having an outer diameter of about 0.190 inch and a wall thickness of about 0.03 inch. Shield 22 is formed of type 303 stainless steel with about the same wall thickness as the outer shaft, and the arcuate member thereof has about twice the radius of curvature of the outer shaft. The length of the frustoconical flange and the arcuate member in the exemplary embodiment are about 0.206 inch and about 0.458 inch, respectively. The irrigating tube 28 in the exemplary embodiment is formed of type 304L stainless steel tubing with an inner diameter of about 0.042 inch, an outer diameter of about 0.058 inch, and a closed distal end proximally spaced about 0.10 inch from the distal end of the shield. Irrigating inlets 36 are shown as longitudinally aligned elongate slots in the exemplary embodiment, with lengths of about 0.094 inch and widths of about 0.025 inch, and with a longitudinal spacing of about 0.03 inch therebetween. Inner shaft 38 in the exemplary embodiment is formed of type 304 stainless steel tubing with an inner diameter of about 0.125 inch and an outer diameter of about 0.146 inch. Tip 40 in the exemplary embodiment is formed of type 303 stainless steel with an outer diameter of about 0.297 inch, an overall length of about 0.589 inch, and an abrasive surface formed over the entire tip by a coating of 40/60 or 60/80 diamond grit. Passages 50 in the exemplary embodiment are about 0.275 inch long and about 0.020 inch wide. An exemplary radial clearance C between the abrading tip and the shield is about 0.06 inch.

The abrading instrument according to the present invention can be configured for use with any powered surgical handpiece including, but not limited to, the Xomed STRAIGHTSHOT® handpiece shown in FIG. 1 and described in U.S. patent application Ser. Nos. 09/005,010, 09/005,012, 09/005,014 and 09/005,189, all filed on Jan. 9, 1998, the disclosures of which are incorporated herein by reference.

The inner and outer members can be made of any suitable medical grade materials but are preferably made of stainless steel. The abrading tip can have any suitable configuration for abrading the outer surface of the skin including, but not limited to, configurations wherein the tip includes brushes, bristles, wire mesh or diamond fraises. When the abrading tip is coated with diamond or other types of grit, the grit can be fine or coarse or can be of any other suitable size. All or part of the outer surface of the abrading tip can be rendered abrasive. While a generally cylindrical abrading tip is shown and described herein, it will be appreciated that any useful shape can be used including, but not limited to, round, conical, frustoconical, pear shaped, and wheel-like shapes.

The abrading tip can be formed with a single aspirating passage or port formed therein or with plural aspirating passages or ports formed therein. The size and shape of the aspirating passages can be varied. For example, the aspirating passages can be elongate slots, circular holes or rectangular apertures.

The irrigating inlets and outlets can have any suitable shape and size including, but not limited to, the slotted configuration shown. The abrading instrument can be formed with a single irrigating inlet and outlet or with plural irrigating inlets and outlets as shown. The abrading instrument can be operated without aspiration or irrigation, with aspiration only, or with irrigation only. Furthermore, an aspirated abrading instrument can be operated without a shield.

The dimensions of the various components described herein are merely exemplary and can be varied dependent upon the nature of the skin defect being treated and the preference of the user. The inner member can be rotated at any suitable speed but is preferably rotated at about 1200 rpm to reduce the possibility of gouging and burning of the skin.

Inasmuch as the present invention is subject to many variations, modifications, and changes in detail, it is intended that all subject matter discussed above or shown in the accompanying drawings be interpreted as illustrative only and not be taken in a limiting sense.

What is claimed is:

1. An abrading instrument for surgically abrading a surface of a skin comprising
    an outer member including an outer shaft having an open distal end, an open proximal end and a lumen between said distal and proximal ends;
    an inner member including an inner shaft having a distal end and a proximal end and an abrading member at said distal end of said inner shaft, said inner member being rotatably disposed within said outer member with said inner shaft disposed in said outer shaft and said abrading member exposed from said outer member, said inner shaft having an aspirating channel therethrough, said abrading member having an abrasive outer surface, and at least one aspirating passage through said abrasive outer surface establishing communication with said aspirating channel from externally of said abrading member, said abrading member being adapted to abrade a surface of the skin contacted by said abrading member while said inner member is rotated relative to said outer member, said aspirating channel being connectible with a source of suction to draw debris generated from abrasion of the skin into said at least one aspirating passage for removal through said aspirating channel; and
    a shield extending distally from said distal end of said outer member and terminating distally at an open distal shield end, said shield extending alongside said abrading member and partially covering said abrading member to contain the debris generated from abrasion of the skin by said abrading member.

2. An abrading instrument as recited in claim 1 wherein said inner shaft is tubular and has a lumen therethrough defining said aspirating channel and said proximal end of said inner shaft is connectible with the source of suction.

3. An abrading instrument as recited in claim 2 wherein said abrading member is formed by a hollow member defining an interior communicating with said lumen of said inner shaft and said at least one aspirating passage is formed in said hollow member to establish communication with said interior from externally of said abrading member.

4. An abrading instrument for surgically abrading a surface of a skin comprising an outer member including an outer shaft having an open distal end, an open proximal end and a lumen between said distal and proximal ends; and an inner member including an inner shaft having a distal end and a proximal end and an abrading member at said distal end of said inner shaft, said inner member being rotatably disposed within said outer member with said inner shaft disposed in said outer shaft and said abrading member exposed from said outer member, said inner shaft having an aspirating channel therethrough, said abrading member having at least one aspirating passage therein establishing communication with said aspirating channel from externally of said abrading member, said abrading member being adapted to abrade a surface of the skin contacted by said abrading member while said inner member is rotated relative to said outer member, said aspirating channel being connectible with a source of suction to draw debris generated from abrasion of the skin into said at least one aspirating passage for removal through said aspirating channel, said inner shaft being tubular and having a lumen therethrough defining said aspirating channel and said proximal end of said inner shaft being connectible with the source of suction, said abrading member being formed by a hollow member defining an interior communicating with said lumen of said inner shaft and said at least one aspirating passage being formed in said hollow member to establish communication with said interior from externally of said abrading member, said abrading member being disposed distally of said distal end of said outer shaft and having a closed distal end and an open proximal end communicating with said distal end of said inner shaft, said hollow member including a rounded end wall defining said closed distal end, a cylindrical portion extending proximally from said end wall and a tapered portion extending proximally from said cylindrical portion to said distal end of said inner shaft, said tapered portion defining said open proximal end of said abrading member and said at least one aspirating passage being formed in said cylindrical portion.

5. An abrading instrument as recited in claim 4 wherein said at least one aspirating passage includes a plurality of aspirating passages formed in said cylindrical portion.

6. An abrading instrument as recited in claim 5 wherein said cylindrical portion has a circumference, each of said aspirating passages is an elongate slot extending longitudinally along said cylindrical portion, said slots being parallel and being angularly spaced from one another around said circumference of said cylindrical portion.

7. An abrading instrument as recited in claim 6 wherein said hollow member has an abrasive outer surface for abrading the surface of the skin.

8. An abrading instrument as recited in claim 7 wherein said hollow member has an exterior and said abrasive outer surface covers the entirety of said exterior.

9. An abrading instrument as recited in claim 8 wherein said abrasive outer surface is formed by a coating of diamond grit.

10. An abrading instrument for surgically abrading a surface of a skin comprising an outer member including an outer shaft having an open proximal end and an open distal end and a shield extending distally from said distal end, said shield terminating distally at an open distal shield end, said outer shaft having a lumen therethrough; and an inner member including an inner shaft having a proximal end and a distal end and an abrading member disposed at said distal end of said inner shaft, said inner member being disposed in said outer member with said inner shaft disposed in said outer shaft and said abrading member disposed alongside said shield so that a portion of said abrading member is covered by said shield and another portion of said abrading member is exposed from said shield to enable contact of said abrading member with a surface of the skin, said inner member being rotatable relative to said outer member to rotate said abrading member relative to said shield, said abrading member being adapted to abrade the surface of the skin contacted by said abrading member when said abrading member is rotated relative to said shield, said shield containing debris generated from abrasion of the skin by said abrading member.

11. An abrading instrument as recited in claim 10 wherein said shield defines an interior communicating with said lumen and said abrading member is disposed in said interior.

12. An abrading instrument as recited in claim 11 wherein said abrading member extends distally from said distal end of said inner shaft and said shield extends distally beyond said abrading member.

13. An abrading member as recited in claim 11 wherein said shield has an inner surface and said abrading member has an outer surface and further including a gap between said outer surface of said abrading member and said inner surface of said shield.

14. An abrading instrument as recited in claim 13 wherein said shield includes an arcuate member extending arcuately at least 180 degrees around said abrading member.

15. An abrading instrument as recited in claim 14 wherein said arcuate member extends arcuately more than 180 degrees around said abrading member.

16. An abrading instrument for surgically abrading a surface of a skin comprising an outer member including an outer shaft having an open distal end, an open proximal end and a lumen between said distal and proximal ends;

an inner member including an inner shaft having a distal end, a proximal end and an abrading member at said distal end of said inner shaft, said inner member being disposed within said outer member with said inner shaft disposed within said outer shaft and said abrading member exposed from said outer member, said inner member being rotatable relative to said outer member to rotate said abrading member, said abrading member being adapted to abrade a surface of the skin contacted by said abrading member and to generate airborne skin debris while said abrading member is rotated;

a shield extending distally from said distal end of said outer member and terminating distally at an open distal shield end, said shield extending alongside said abrading member and partially covering said abrading member to contain the debris generated from abrasion of the skin by said abrading member;

an irrigating port extending along said outer member and having a proximal end connectible with a source of irrigating fluid and at least one irrigating outlet disposed adjacent said abrading member through which the irrigating fluid is discharged toward said abrading member;

an aspirating channel through said inner member connectible with a source of suction; and at least one aspirating passage in said abrading member establishing communication with said aspirating channel from externally of said abrading member whereby the airborne skin debris generated from abrasion of the surface of the skin is evacuated through said aspirating channel.

17. An abrading instrument as recited in claim 16 wherein said abrading member extends distally from said distal end of said inner shaft, said abrading member having a portion covered by said shield and having another portion exposed from said shield to enable contact of said abrading member with the surface of the skin.

18. An abrading instrument as recited in claim 17 wherein said irrigating port includes an irrigating tube extending longitudinally along said inner member, said irrigating tube having a closed distal end adjacent said shield, said shield being disposed between said irrigating tube and said abrading member, said shield having at least one irrigating inlet therein communicating with said at least one irrigating outlet whereby the irrigating fluid is discharged through said irrigating inlet toward said abrading member.

19. An abrading instrument as recited in claim 18 wherein said at least one aspirating passage is aligned with said at least one irrigating inlet as said abrading member is rotated.

20. An abrading instrument assembly for surgically abrading a surface of a skin comprising an abrading instrument including an outer member and an inner member rotatably disposed in said outer member, said outer member including a tubular outer shaft having an open distal end and an open proximal end, said inner member including an inner shaft having a distal end and a proximal end and an abrading member at said distal end of said inner shaft, said inner shaft having a lumen therethrough, said inner shaft being disposed in said outer shaft with said abrading member exposed from said outer member, said abrading member having an abrasive outer surface and at least one aspirating passage through said abrasive outer surface establishing communication with said lumen from externally of said abrading member, said abrading member being adapted to abrade a surface of the skin contacted by said abrading member while said inner member is rotated within said outer member; and a powered surgical handpiece releasably connected with said proximal ends of said outer and inner shafts, respectively, said handpiece being adapted to rotate said inner member relative to said outer member, said handpiece including a suction port connectible with a source of suction to establish suction in said lumen whereby debris generated from abrasion of the skin is drawn into said at least one aspirating passage for evacuation through said lumen and said handpiece.

21. An abrading instrument assembly as recited in claim 20 wherein said outer member further includes a shield extending distally from said distal end of said outer shaft and disposed over a portion of said abrading member to contain the debris generated from abrasion of the skin.

22. An abrading instrument assembly as recited in claim 21 and further including an irrigating port extending along said outer member and having a proximal end connectible with a source of irrigating fluid and an irrigating outlet adjacent said abrading member through which the irrigating fluid is discharged toward said abrading member.

23. A method of dermabrasion comprising the steps of rotating an abrading member of an abrading instrument alongside a shield of the abrading instrument;

positioning the abrading instrument such that the abrading member is disposed between the shield and a surface of the skin to be abraded;

contacting the surface of the skin with a portion of the abrading member exposed from the shield;

abrading the surface of the skin with the abrading member;

containing debris, produced by abrasion of the skin, with the shield; and aspirating the debris through the abrading member.

24. The method of dermabrasion as recited in claim 23 and further including the step of wetting the debris to promote containment thereof.

25. The method of dermabrasion as recited in claim 24 wherein said step of wetting includes discharging irrigating fluid adjacent the abrading member via an irrigating port of the abrading instrument.

26. A method of dermabrasion comprising the steps of rotating an inner member of an abrading instrument within an outer member of the abrading instrument to rotate an abrading member of the inner member that is exposed from the outer member;

contacting an outer surface of the skin with the rotating abrading member;

abrading the outer surface of the skin with the rotating abrading member; and aspirating debris, produced by abrasion of the skin, through the inner member.

27. The method of dermabrasion as recited in claim 26 wherein the inner member includes a shaft, the abrading member is disposed at a distal end of the shaft and said step of aspirating includes aspirating the debris into the abrading member and through the shaft.

28. The method of dermabrasion as recited in claim 27 and further including the step of discharging an irrigating fluid adjacent the abrading member.

29. The method of dermabrasion as recited in claim 26 and further including the step of containing the debris with a shield of the outer member.

30. The method of dermabrasion as recited in claim 26 wherein said step of rotating includes rotating the inner member with a powered surgical handpiece coupled to the inner and outer members.

31. The method of dermabrasion as recited claim 30 wherein said step of aspirating includes aspirating the debris through the powered surgical handpiece.

32. An abrading instrument for surgically abrading a surface of a skin comprising an outer member including an outer shaft having an open distal end, an open proximal end and a lumen between said distal and proximal ends;

an inner member including an inner shaft having a distal end and a proximal end and an abrading member at said distal end of said inner shaft, said inner member being rotatably disposed within said outer member with said inner shaft disposed in said outer shaft and said abrading member exposed from said outer member, said inner shaft having an aspirating channel therethrough, said abrading member having at least one aspirating passage therein establishing communication with said aspirating channel from externally of said abrading member, said abrading member being adapted to abrade a surface of the skin contacted by said abrading member while said inner member is rotated relative to said outer member, said aspirating channel being connectible with a source of suction to draw debris generated from abrasion of the skin into said at least one aspirating passage for removal through said aspirating channel, said inner shaft being tubular and having a lumen therethrough defining said aspirating channel and said proximal end of said inner shaft being connectible with the source of suction, said abrading member being formed by a hollow member defining an interior communicating with said lumen of said inner shaft and said at least one aspirating passage being formed in said hollow member to establish communication with said interior from externally of said abrading member, said abrading member being disposed distally of said distal end of said outer shaft and having a closed distal end and an open proximal end communicating with said distal end of said inner shaft; and a shield extending distally from said distal end of said outer member and terminating distally at an open distal shield end, said shield extending alongside said abrading member and partially covering said abrading member to contain the debris generated from abrasion of the skin by said abrading member.

33. An abrading instrument for surgically abrading a surface of a skin comprising an outer member including an outer shaft having an open proximal end and an open distal end and a shield extending distally from said distal end, said outer shaft having a lumen therethrough;

an inner member including an inner shaft having a proximal end and a distal end and an abrading member disposed at said distal end of said inner shaft, said inner member being disposed in said outer member with said inner shaft disposed in said outer shaft and said abrading member disposed alongside said shield so that a portion of said abrading member is covered by said shield and another portion of said abrading member is exposed from said shield to enable contact of said abrading member with a surface of the skin, said inner member being rotatable relative to said outer member to rotate said abrading member relative to said shield, said abrading member being adapted to abrade the surface of the skin contacted by said abrading member when said abrading member is rotated relative to said shield, said shield containing debris generated from abrasion of the skin by said abrading member, said shield defining an interior communicating with said lumen and said abrading member being disposed in said interior, said shield having an inner surface and said abrading member having an outer surface, said shield including an arcuate member extending arcuately at least 180 degrees around said abrading member, said arcuate member terminating distally at an arcuate distal edge defining a distal end of said shield, said shield further including a tapered flange extending proximally from said arcuate member to said distal end of said outer shaft; and a gap between said outer surface of said abrading member and said inner surface of said shield.

34. An abrading instrument as recited in claim 33 wherein said abrading member includes a cylindrical portion and a tapered portion extending proximally from said cylindrical portion to said distal end of said inner shaft, said tapered flange forming a stop for said tapered portion limiting longitudinal proximal movement of said inner member relative to said outer member.

35. An abrading instrument as recited in claim 34 wherein said cylindrical portion has an outer surface, said arcuate member has an inner surface and said gap is defined between said outer surface of said cylindrical portion and said inner surface of said arcuate member.

36. An abrading instrument as recited in claim 35 wherein said outer surface of said abrading member is abrasive.

37. An abrading instrument for surgically abrading a surface of a skin comprising an outer member including an outer shaft having an open distal end, an open proximal end and a lumen between said distal and proximal ends;

an inner member including an inner shaft having a distal end, a proximal end and an abrading member at said distal end of said inner shaft, said inner member being disposed within said outer member with said inner shaft disposed within said outer shaft and said abrading member exposed from said outer member, said inner member being rotatable relative to said outer member to rotate said abrading member, said abrading member being adapted to abrade a surface of the skin contacted by said abrading member while said abrading member is rotated, said abrading member extending distally from said distal end of said inner shaft and said outer member further including a shield extending distally from said distal end of said outer shaft to cover a portion of said abrading member, said abrading member having another portion exposed from said shield to enable contact of said abrading member with the surface of the skin, said shield adapted for containing debris generated from abrasion of the skin by said abrading member;

an irrigating port extending along said outer member and having a proximal end connectible with a source of irrigating fluid and at least one irrigating outlet disposed adjacent said abrading member through which the irrigating fluid is discharged toward said abrading member, said irrigating port including an irrigating tube extending longitudinally along said inner member, said irrigating tube having a closed distal end adjacent said shield, said shield being disposed between said irrigating tube and said abrading member, said shield having at least one irrigating inlet therein communicating with said at least one irrigating outlet whereby the irrigating fluid is discharged through said irrigating inlet toward said abrading member, said at least one irrigating outlet including a plurality of irrigating outlets spaced longitudinally along said irrigating tube and said at least one irrigating inlet includes a plurality of irrigating inlets spaced longitudinally along said shield in alignment with said plurality of irrigating outlets, respectively;

an aspirating channel through said inner member connectible with a source of suction; and at least one aspirating passage in said abrading member establishing communication with said aspirating channel from externally of said abrading member whereby debris generated from abrasion of the surface of the skin is evacuated through said aspirating channel, said at least one aspirating passage being aligned with said at least one irrigating inlet as said abrading member is rotated.

38. An abrading instrument as recited in claim 37 wherein said abrading member includes a hollow member having a closed distal end, a cylindrical portion extending proximally from said closed distal end of said hollow member and a tapered portion extending proximally from said cylindrical portion to said distal end of said inner shaft, said at least one aspirating passage includes a plurality of aspirating passages formed in said cylindrical portion at angularly spaced locations therearound, each of said aspirating passages being aligned with said plurality of irrigating inlets as said abrading member is rotated.

39. An abrading instrument as recited in claim 38 wherein said irrigating tube extends externally along said outer member.

* * * * *